United States Patent [19]

Chen et al.

[11] 4,427,770

[45] Jan. 24, 1984

[54] HIGH GLUCOSE-DETERMINING ANALYTICAL ELEMENT

[75] Inventors: Shuenn-tzong Chen; Mark J. Sherwood; Mary E. Warchal, all of Elkhart, Ind.

[73] Assignee: Miles Laboratories, Inc., Elkhart, Ind.

[21] Appl. No.: 388,123

[22] Filed: Jun. 14, 1982

[51] Int. Cl.³ .................... G01N 33/66; G01N 33/52
[52] U.S. Cl. ...................................... 435/14; 422/56; 435/28; 435/805; 436/95
[58] Field of Search ................. 435/14, 28, 805; 422/56; 436/95

[56] References Cited

U.S. PATENT DOCUMENTS

| | | | |
|---|---|---|---|
| 4,098,574 | 7/1978 | Dappen | 435/14 |
| 4,247,631 | 1/1981 | Nix | 435/14 X |
| 4,251,629 | 2/1981 | Yamanisi | 435/14 X |
| 4,303,753 | 12/1981 | Lam | 435/14 |
| 4,350,762 | 9/1982 | Luca | 435/14 X |

OTHER PUBLICATIONS

D. Barham et al., Analyst, 97, 142–145 (1972).
P. Fossati et al., Clin. Chem., 26 (2), 227–231 (1980).
Chemical Abstracts, 95: 38684a (1981).
P. Trinder, Ann. Clin. Biochem., 6, 24–27 (1969).

Primary Examiner—Sidney Marantz
Attorney, Agent, or Firm—Roger N. Coe

[57] ABSTRACT

An analytical element for quantitatively determining high levels of glucose in blood is made by (a) impregnating a carrier with a first solution, having dissolved therein 4-aminoantipyrine and 3-hydroxy-2,4,6-triiodobenzoic acid or 3,5-dichloro-2-hydroxy-benzene sulfonic acid or salts thereof, a glucose oxidase and a peroxidase, and drying the carrier; and (b) applying to the carrier a second solution of a film-forming agent in a volatile solvent, and drying to remove the volatile solvent and leave a film over the dried first impregnant.

11 Claims, No Drawings

HIGH GLUCOSE-DETERMINING ANALYTICAL ELEMENT

BACKGROUND OF THE INVENTION

1. Field of the Invention

The present invention relates generally to the field of diagnostic tests and, more particularly, to test devices and elements useful in the quantitative determination of an analyte having a high glucose content.

2. Brief Description of the Prior Art

Test devices in the form of test strips and similar solid phase analytical elements have become commonplace in the analysis of various types of samples, particularly biological fluids. Test strips designed for detecting sugar, i.e., glucose, in biological fluids, such as serum and urine, have been advantageous in the diagnosis of disease.

U.S. Pat. No. 4,273,868, commonly assigned herewith, discloses a composition, a test device, a method of making the test device and a process for determining glucose in a sample. The test composition comprises glucose oxidase, a peroxidatively active substance such as peroxidase, a stabilizing agent and a 3,3',5,5'-tetraalkylbenzidine indicator in an amount sufficient to rapidly produce, upon contact of the test means with a predetermined amount of a glucose-containing sample, a stable colored reaction product believed to comprise reduced and oxidized forms of said indicator in stable equilibrium. Preferably, 3,3',5,5'-tetramethylbenzidine is present in a concentration of at least about 2.6 millimoles per thousand International Units of glucose oxidase activity. One of the disclosed stabilizing agents is an interpolymer of methylvinyl ether and maleic anhydride, marketed commercially as Gantrez AN-139 by GAF Corporation. The test devices are prepared by a two-dip impregnation process where the 3,3',5,5'-tetraalkylbenzidine is impregnated in the second dip using a solution thereof prepared in an organic solvent.

U.S. Application Ser. No. 292,345, filed Aug. 13, 1981, now U.S. Letters Pat. No. 4,361,648, discloses an improvement thereover wherein a carrier is impregnated with an aqueous solution of tetraalkylbenzidine dihydrochloride and polymeric mordant and dried, then impregnated with a solution of a glucose oxidase and peroxidase, and then impregnated with a solution of a film-forming agent in a volatile solvent. Such test strip is quite satisfactory for the instrumental determination of glucose levels from 0–4000 milligrams per liter(mg/liter). Such strip, however, is not suitable for visual determination of relatively high glucose levels since the color differences are inadequate.

Bahan and Trinder in Analyst, February 1972, Vol. 97, pages 142–145, Trinder in Ann. Clin. Biochem, 6 (1969) 24–27, and Fossati et al in Clin. Chem, 26/2 (1980) 227–231 discuss using 4-aminoantipyrine as a color coupler with 3,5-dichlorohydroxybenzensulfonic acid in determining glucose levels using glucose oxidase/peroxidase system. This test is a liquid assay and is used primarily for glucose concentration between 0–4000 mg/liter. In this test, whole blood is added to a protein precipitant solution and centrifuged. The clear fluid is added to the color reagent, incubated at 30° C. for 15 minutes and then the optical density is read at 515 nanometers(nm) by a spectrophotometer. This liquid system results in expected kinetics and is slow.

It is accordingly an object of the invention to provide an improved test strip which involves an atypical kinetic system, reacts quickly to permit visual quantitative glucose determination over the range from about 2000 to 8000 mg/liter, and which strip is simple and inexpensive to prepare.

SUMMARY OF THE INVENTION

These and other objects and advantages are realized in accordance with the present invention pursuant to which there is provided an analytical element produced by the steps of (a) impregnating a carrier with a first solution, having dissolved therein 4-aminoantipyrine, or a salt thereof, and 3-hydroxy-2,4,6-triiodo-benzoic acid or 3,5-dichloro-2-hydroxy-benzene sulfonic acid, or salts thereof, a glucose oxidase and a peroxidase, and drying the carrier; and (b) applying to the carrier a second solution of a film-forming agent in a volatile solvent, and drying to remove the volatile solvent and leave a film over the dried first impregnant.

In accordance with another aspect of the invention, such an element is used in conjunction with a conventional second element which quantifies glucose contents below about 1800 mg/liter. Thus, if the second element indicates a glucose level beyond its range the technician then uses the first element.

Likewise there is provided an analytical element and method for the determination of an analyte in a fluid sample which comprises contacting a sample with the analytical element according to the invention and observing any resultant color change. The colored reaction product is produced within a time period of about 60–90 seconds after contact of the analytical element with the body fluid sample to be tested.

DESCRIPTION OF THE PREFERRED EMBODIMENTS

Although specific terms are used in the following description for the sake of clarity, these terms are intended to refer only to the particular embodiment of the invention selected for exemplary illustration, and are not intended to define or limit the scope of the invention.

ANALYTE-RESPONSIVE COMPONENT

The analyte-responsive component comprises those reagents which interact with the analyte and/or resulting products thereof to produce an oxidizing substance, e.g., hydrogen peroxide. In the presence of a peroxidatively active substance, which is one reagent of the analyte-responsive component, the oxidizing substance oxidizes the indicator to produce a detectable species thereof.

The indicator coupling agent comprises 4-aminoantipyrine(AAP) and 3,5-dichloro-2-hydroxy-benzene sulfonic acid and salts thereof. As an alternative, 3-hydroxy-2,4,6-triiodobenzoic acid (mw 515.8) can be substituted for the 3,5-dichloro-2-hydroxy-benzene sulfonic acid. Attempts to use tetraalkylbenzidines as the indicator were unsuccessful because they lack the necessary reaction kinetics properties. 3-Methyl-2-benzothiazolinone hydrazone(MBTH) with primiquine diphosphate was unsuitable. 4-aminoantipyrine with coupling agents 3-hydroxy-1,2,3,4-tetrahydrobenzo(n)quinoline(HTBQ), methyl catechol, primiquine diphosphate and phenothiazine was also unsuitable.

The combination of 4-aminoantipyrine and 3,5-dichloro-2-hydroxy-benzene sulfonic acid, and the sodium or potassium salts thereof, performs successfully and best at particular ratios, as well as enzyme levels, buffer concentrations and polymer mordants to monitor the color formation so that essentially no color is generated with a glucose concentration less than 1800 mg/liter and then a slight peach color starts to form around 2000 mg/liter and continues to produce more color until 8000 mg/liter. As a result, good color resolution exists in every adjacent color block.

POLYMERIC MORDANT

Suitable polymeric mordants which can be used include poly(carboxylic acids) having the formula:

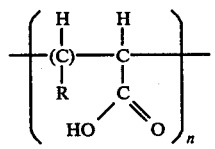

wherein R is a $C_1$–$C_{18}$ alkyl or amide, and n is an integer from 2 to the total number of repeating units of the polymer. Examples include polyacrylic acid and polyacrylamide copolymer.

Other polymeric mordants which can be used are copolymeric anhydrides having the formula:

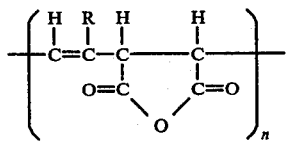

wherein R is $C_1$–$C_{18}$ alkyl, ether, acetate or benzyl and n is an integer from 2 to the total number of repeating units of the polymer. Examples include methyl vinyl ether maleic anhydride copolymer; vinyl acetate-maleic anhydride copolymer; ethylene-maleic anhydride copolymer; octadecyl vinyl ether-maleic anhydride copolymer; and styrene maleic anhydride copolymer.

The polymeric mordant is preferably present in a concentration of from about 0.5 to about 0.75 percent of the composition on a weight to weight basis.

CARRIER

The term carrier refers to matrices which are insoluble in and maintain their structural integrity when exposed to physiological or other liquid to be tested. Suitable matrices which can be used include paper, cellulose, wood, synthetic resin fleeces, glass fiber, nonwoven and woven fabrics, gelatin, various organic polymers, such as polypropylene, and other organic materials well known as film formers to those skilled in the art. For convenience, the carrier can be suitably attached to an insoluble support or handle member which can be made from polystyrene.

ELEMENT PREPARATION

As recited hereinabove, the test device is prepared by a process which comprises impregnating the carrier with a first solution having dissolved therein the indicator-coupling agent and a glucose oxidase-peroxidase. The glucose oxidase-peroxidase is described more fully in Application Ser. No. 292,345, supra, the disclosure of which is incorporated by reference.

Using Whatman 3MM paper, the concentration of the 4-aminoantipyrine or salt thereof in the first solution is from about 5 to 40, preferably about 10 to 30, and most preferably about 15 millimoles/liter(mmoles/liter), while the concentration of the 3,5-dichloro-2-hydroxy-benzene sulfonic acid or salt thereof is from about 0.5 to 500, preferably about 1 to 50, and most preferably about 6 mmoles/liter.

The solution is advantageously buffered to a pH of about 5 to 8, preferably about 7, employing a known noninterfering buffer such as tris-malonate. Citrate or any other buffer which will provide the same pH range can be used.

Drying is of course effected as quickly as possible.

The second step in element preparation comprises impregnating the carrier with a solution of a semipermeable polymer, such as ethyl cellulose, in an organic solvent and drying the carrier. The organic solvent preferably includes toluene. Particularly preferred is an organic solvent which includes toluene and ethanol. Where the solvent consists essentially of toluene and ethanol, the toluene is from about 80 to 95 percent of the solvent and the ethanol is from about 5 to about 20 percent of the solvent, the toluene and ethanol being together 100 percent on a volume/volume basis.

Suitable film-forming agents include other hydrophobic cellulose ethers and esters, the film serving to prevent formed elements (red blood cells) from absorbing into the carrier during the period of use.

ANALYTICAL PROCEDURE

The test device is advantageously used by momentarily dipping it in a test sample or by otherwise introducing a test sample onto the carrier matrix, whereby a detectable color change results when glucose is present. The volumetric capacity of the carrier serves to limit the amount of sample absorbed thereby and to which the test means incorporated therewith is exposed. Any excess sample can be removed by washing the carrier to thereby limit the amount of sample tested to the volume thereof which has actually entered the carrier matrix. The liquid medium to be assayed can be a naturally occurring or artificially formed liquid suspected to contain the ligand, and usually is a biological fluid or dilution thereof. Biological fluids that can be assayed include serum, plasma, urine, saliva, and amniotic and cerebrospinal fluids. The test device can be used in the same way when samples of plasma, serum or other body fluids are tested.

Semi quantitative results can be obtained using the analytical element of the present invention by comparing the color produced with a panel of standard colors obtained with known concentrations of analyte employing the same indicator.

The key issue involving the chemistry of the novel elements is that it yields reaction kinetics which are atypical compared to test systems with other indicators in solid or liquid-phase; and even the same components in liquid-phase or in solid-phase with a different composition.

Because of these atypical kinetics, the element is unresponsive to glucose levels below about 1500 mg/liter, and so is still quite light in color at 2000 mg/liter, the beginning of its intended use range; above this level, typical reaction kinetics occur, and higher glucose levels are readily quantitated. In contrast, any other system which displays more typical reaction kinetics will either (a) be so dark at high glucose levels that visual quantitation at high levels is difficult, or (b) be so unreactive in order still to be light in appearance at glucose levels of about 2000 mg/liter that again it will not yield easily quantitated visual differences at various high levels.

EXAMPLE

The example shown is merely illustrative and not to be construed as a limitation of the invention. One skilled in the art will be able to make such variations, substitutions and changes in the ingredients and parameters as may seem desirable. Peroxidase (9105MR-horseradish-)and glucose oxidase(9400MR from *Aspergillus niger*) used in the examples were obtained from the Research Products Division, Miles Laboratories, Inc., Elkhart, IN. Gantrez AN 139 was obtained from GAF Corp., Chemical Products, N.Y., N.Y. The activity of the enzyme preparation is measured by the number of units of activity per milligram of dry weight. The Commission on Enzymes of the International Union of Biochemistry has defined an International Unit (I.U.) of enzyme activity as 1 micromole (umol) of substrate utilized per minute under specified conditions of pH and temperature control.

Example I—Analytical Element for Glucose Assay

In the experiments reported by this example an analytical element was prepared by the method according to the invention and tested for its ability quantitatively to determine visually the presence of glucose in a liquid sample. Gantrez AN-139, a polycarboxylic anion (chemically it is the interpolymer of methyl vinyl ether and maleic anhydride), was added in the first dip. The Gantrez behaves as a dye mordant, so forming a complex, in the system, thereby protecting final colored reaction product. Ethyl cellulose in toluene was used as the second dip.

Element Preparation

The solutions used in preparing the glucose specific element contained the following components:

| First Dip, for every 100 milliliters (ml) | |
| --- | --- |
| 4-AAP | 0.36 grams (g) |
| Gantrez (2%) | 25 ml |
| Tris-Malonate Buffer, pH + 7.4 | 20 ml |
| H$_2$O | 55 ml |
| 3,5-Dichloro-2-hydroxy-benzene sulfonate sodium salt | 0.12 g |
| Peroxidase | 0.2 g |
| Glucose Oxidase (1000 IU/l) | 6.0 ml |
| Second Dip, for every 100 ml | |
| Ethocel (ethyl cellulose) | 1.5 g |
| Toluene | 95 ml |
| Ethyl Alcohol | 5 ml |

Reagent-containing Whatman 3MM filter paper (Whatman, Inc., Clifton, N.J.) is prepared by (a) impregnating sheets of the paper to saturation with the first solution and drying the paper at 60° Centigrade (C) for 10 minutes; (b) impregnating the paper of (a) to saturation with the second solution and drying at 40° C. for 10 minutes.

The reagent-containing paper was cut to 0.5 cm (centimeter) × 1.0 cm dimensions and fixed to one end of a 0.5 cm × 8.25 cm polystyrene film by double-faced adhesive tape, providing devices according to the invention. These were stored with a dessicant in brown glass bottles until used.

Test Solutions

Fresh blood collected into evacuated collection tubes containing ethylene diamine tetraacetic acid (EDTA) was metabolically depleted of glucose by incubation at 37° C. overnight (16–20 hours). The hematocrit was adjusted to about 45%. Various glucose levels were prepared by adding various amounts of stock glucose (10% w/v) into the blood samples.

Analytical Procedure

The performance of the reagent device prepared and incubated as above-described was analyzed by the following procedure:

(a) A large drop of capillary or venous blood sufficient to cover each reagent area is applied to the test device.

(b) Sixty seconds are allowed to elapse.

(c) Each reagent area is then washed with water sufficiently to remove the blood sample.

(d) Each reagent area is then blotted with a lint-free paper towel.

(e) The low range pad or reagent(area) is then compared with color blocks in the range of 200 to 1,800 mg/liter. The color blocks for this range have a greenish tint and if the color produced falls between two color blocks the value is interpolated. If the color matches or exceeds the color of the 1,800 mg/liter color block, another 30 seconds is allowed to elapse before comparing the resulting color of the high range pad or reagent area with color blocks for the high range (2,000 to 8,000 mg/liter), again the interpolating if the color produced falls between two color blocks. The high range color blocks have a peach or orange tint in contrast to the green tint of the low range color blocks.

EXAMPLE II

Another suitable analytical element for the high range glucose levels was prepared by substituting in Example I 0.06 g of 3-hydroxy-2,4,6-triiodobenzoic acid for the 3,5-dichloro-2-hydroxy-benzen sulfonate, sodium salt and substituting 0.18 g of 4-AAP.HCl for the 4-AAP. Essentially equivalent results were obtained.

It will be understood that the specification and examples are illustrative but not limitative of the present invention and that other embodiments within the spirit and scope of the invention will suggest themselves to those skilled in the art.

What is claimed is:

1. A method for preparing an analytical element for determining glucose in a liquid sample which method comprises the steps of (a) impregnating a carrier with a first solution having dissolved therein 4-aminoantipyrine or a salt thereof and 3-hydroxy-2,4,6-triiodobenzoic acid or 3,5-dichloro-2-hydroxy-benzene sulfonic acid, or a salt thereof, a glucose oxidase and a peroxidase, and drying the carrier; and (b) applying to the carrier a second solution of film-forming agent in a volatile solvent, and drying to remove the volatile solvent and leave a film over the dried first impregnant.

2. A method according to claim 1, wherein the concentration of the 4-aminoantipyrine or salt thereof in the first solution is from about 5 to 40 mmoles/liter.

3. A method according to claim 1, wherein the concentration of the 3-hydroxy-2,4,6-triiodobenzoic acid or 3,5-dichloro-2-hydroxybenzene sulfonic acid, or salt thereof, in the first solution is from about 0.5 to 500 mmoles/liter.

4. A method according to claim 1, wherein the film-forming agent in the second solution is a hydrophobic cellulose ether or ester.

5. A method according to claim 1, wherein the first solution contains a buffer for maintaining a pH from about 5 to 8 and a mordant.

6. A method according to claim 5, wherein the concentration of the 4-aminoantipyrine or salt thereof in the first solution is from about 10 to 30 mmoles/liter and the concentration of the 3,5-dichloro-2-hydroxybenzene sulfonic acid or salt thereof in the first solution is from about 1 to 50 mmoles/liter.

7. A method according to claim 5, wherein the concentration of the 4-aminoantipyrine or salt thereof in the first solution is about 15 mmoles/liter, the concentration of the 3,5-dichloro-2-hydroxybenzene sulfonic acid or salt thereof in the first solution is about 6 mmoles/liter, and the film-forming agent in the second solution is a hydrophobic cellulose ether or ester.

8. A method according to claim 5, wherein the 4-aminoantipyrine is present in the first solution as the hydrochloride, the sulfonic acid is present in the first solution as the sodium salt, the solvent in the first solution is water, the pH of the first solution is about 7 and it contains a polymeric polycarboxylic acid or anhydride thereof as the mordant, and the film-forming agent in the second solution is ethyl cellulose.

9. An analytical element for determining whole blood glucose produced by the process of claim 1.

10. A method for determining the glucose content of whole blood within the range of about 2000 to 8000 mg/liter comprising contacting the whole blood with an analytical element produced by the process of claim 1, and matching the resulting color of the element with predetermined standards.

11. A system for determining the glucose content of whole blood over a range from about 0 to 8000 mg/liter comprising, in combination, an element for identifying a glucose content of up to about 2000 mg/liter, and the analytical element produced by the process of claim 1.

* * * * *